(12) United States Patent
Lyu et al.

(10) Patent No.: US 8,268,458 B2
(45) Date of Patent: Sep. 18, 2012

(54) CARBAZOLE COMPOUNDS AND ORGANO-ELECTROLUMINESCENT DEVICES USING THE SAME

(75) Inventors: Yi-yeol Lyu, Yongin-si (KR); Kook-heon Char, Seoul (KR); Chang-hee Lee, Seoul (KR); Jeong-hun Kwak, Seoul (KR)

(73) Assignee: Samsung Electronics Co., Ltd. (KR)

( * ) Notice: Subject to any disclaimer, the term of this patent is extended or adjusted under 35 U.S.C. 154(b) by 357 days.

(21) Appl. No.: 12/606,851

(22) Filed: Oct. 27, 2009

(65) Prior Publication Data

US 2010/0181900 A1 Jul. 22, 2010

(30) Foreign Application Priority Data

Jan. 22, 2009 (KR) .................. 10-2009-0005569

(51) Int. Cl.
*H01L 51/54* (2006.01)

(52) U.S. Cl. ........ 428/690; 428/917; 313/504; 313/505; 313/506; 257/40; 257/E51.05; 257/E51.032

(58) Field of Classification Search ............... 428/690, 428/917; 548/440; 546/440, 79; 313/504, 313/505, 506; 257/40, E51.05, E51.032
See application file for complete search history.

(56) References Cited

U.S. PATENT DOCUMENTS

2005/0084711 A1* 4/2005 Sasaki et al. .................. 428/690
2007/0099025 A1   5/2007 Oshiyama et al.

FOREIGN PATENT DOCUMENTS

JP         2008-137978 A     6/2008

* cited by examiner

*Primary Examiner* — Jennifer Chriss
*Assistant Examiner* — Gregory Clark
(74) *Attorney, Agent, or Firm* — Cantor Colburn LLP

(57) ABSTRACT

A carbazole compound represented by Formula 1:

Formula 1

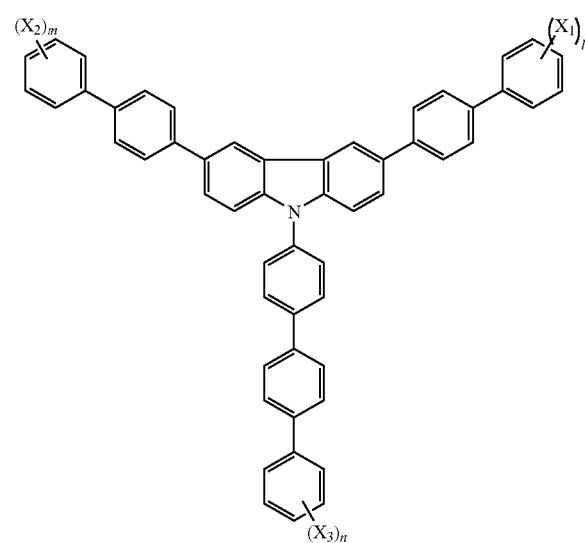

wherein $X_1$, $X_2$ and $X_3$ are each independently selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 0 to 5.

11 Claims, 1 Drawing Sheet

CARBAZOLE COMPOUNDS AND ORGANO-ELECTROLUMINESCENT DEVICES USING THE SAME

CROSS-REFERENCE TO RELATED APPLICATION

This application claims priority to Korean Patent Application No. 10-2009-0005569, filed on Jan. 22, 2009, and all the benefits accruing therefrom under 35 U.S.C. §119, the content of which in its entirety is herein incorporated by reference.

BACKGROUND

1. Field

One or more embodiments relate to a carbazole compound and an organo-electroluminescent device using the same, and more particularly, to a carbazole compound capable of forming a high-quality organic layer and an organo-electroluminescent device having excellent internal and external luminescence efficiency and high color purity using the carbazole compound.

2. Description of the Related Art

Organo-electroluminescent devices include a first electrode, a second electrode and at least one organic layer interposed between the first and second electrodes. The organic layer may be classified as vacuum deposited materials or solution coated materials depending on the method used to prepare the organic layer. The vacuum deposited materials may have a vapor pressure of greater than or equal to $10^{-6}$ torr at a temperature of less than or equal to 500° C. and may comprise a low molecular weight material having a molecular weight of less than or equal to 1200 Daltons. The solution-coated materials may be highly soluble in a solvent to facilitate preparation of a solution of the materials, and may include an aromatic or heterocyclic group.

Use of vacuum deposition processes in the manufacture of organo-electroluminescent devices may increase costs. When a shadow mask is used to manufacture pixels for displays producing natural colors, the pixels may not provide high resolution. On the other hand, when organo-electroluminescent devices are manufactured using a solution coating method such as inkjet printing, screen printing or spin coating, organic layers may be readily formed, which may reduce manufacturing costs. In addition, organo-electroluminescent devices manufactured using solution coating may have higher resolution than organo-electroluminescent devices manufactured using a shadow mask.

One drawback of solution coating methods is that the materials used in solution coatings have poorer thermal stability and lower color purity than those used in vacuum deposition. In addition, the materials used in solution coatings may crystallize, and the crystal size may be commensurate with a wavelength of visible light. Thus a white residue may form due to scattering of visible light by the crystals or pin holes may be formed, which may degrade desirable properties of the organic-electroluminescent devices.

Thus, there is still a need to develop an organo-electroluminescent device having low driving voltage, excellent luminescence brightness, high luminescence efficiency and high color purity. There further remains a need for developing an organic compound capable of forming an organic layer by solution coating for use in the organo-electroluminescent device, where the compound has excellent thermal stability and high color purity.

SUMMARY

One or more embodiments include a carbazole compound having excellent thermal stability and light emitting capability in which charges are readily transported and which may be manufactured by a dry or a wet process.

One or more embodiments include an organo-electroluminescent device having excellent luminescence efficiency, low driving voltage and high color purity.

Additional aspects, features and advantages will be set forth in the description which follows.

According to one or more embodiments, there is provided a carbazole compound represented by Formula 1:

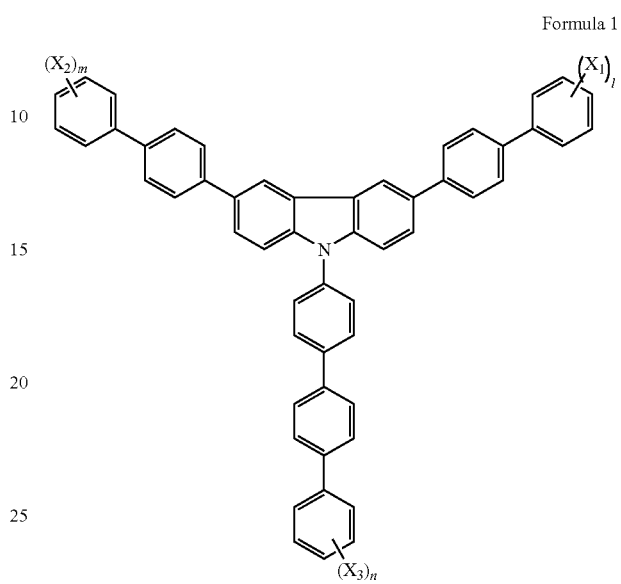

Formula 1 wherein $X_1$, $X_2$ and $X_3$ are each independently selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 0 to 5.

According to one or more embodiments, there is provided an organo-electroluminescent device comprising: a first electrode; a second electrode; and at least one layer interposed between the first electrode and the second electrode, wherein the at least one layer comprises a carbazole compound represented by Formula 1:

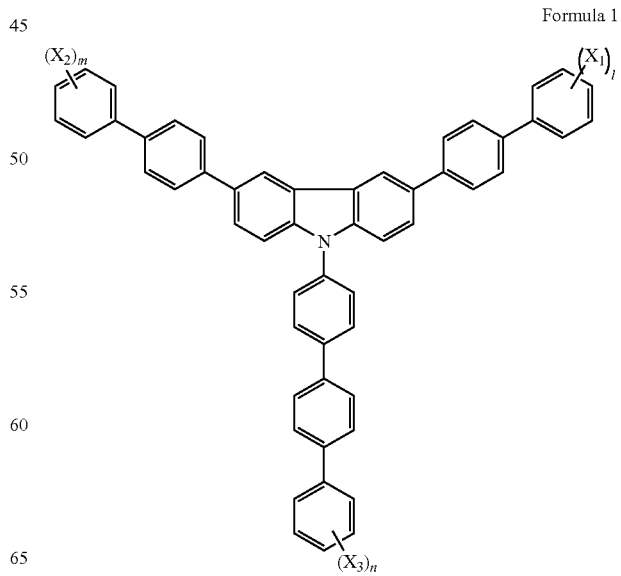

Formula 1 wherein $X_1$, $X_2$ and $X_3$ are each independently selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 0 to 5.

Also disclosed is a method of manufacturing an organo-electroluminescent device, the method comprising: disposing first electrode; disposing a second electrode; and disposing a layer between the first electrode and the second electrode, wherein the layer comprises a carbazole compound represented by Formula 1:

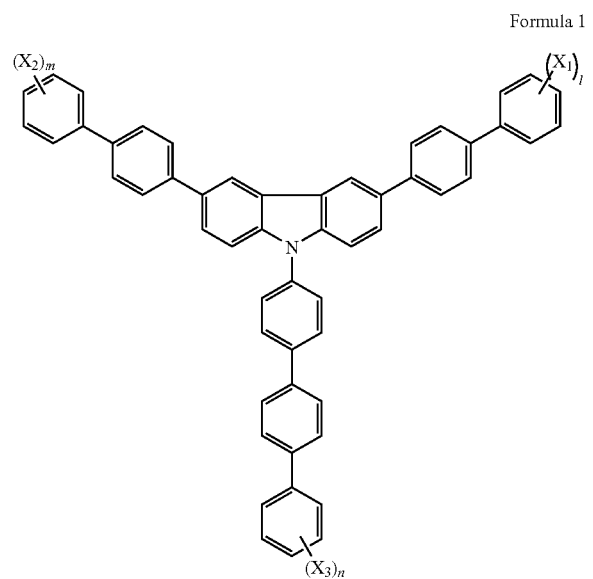

Formula 1 wherein $X_1$, $X_2$ and $X_3$ are each independently selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 0 to 5.

BRIEF DESCRIPTION OF THE DRAWINGS

These and/or other aspects, features and advantages will become apparent and more readily appreciated from the following description of the embodiments, taken in conjunction with the accompanying drawings in which.

DETAILED DESCRIPTION

Figure 1A:
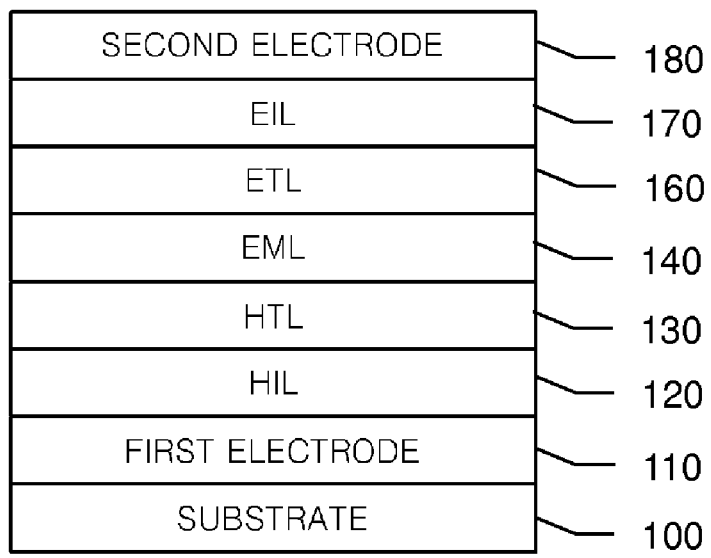
FIGS. 1A and 1B are schematic sectional views illustrating an exemplary embodiment of an organo-electroluminescent device.

Reference will now be made in further detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects, features and advantages of the present description.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The term "substituted," as used herein, means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into a solution for coating. Unless otherwise specified, substituents are named into the core structure. For example, it is to be understood that when (cycloalkyl)alkyl is listed as a possible substituent, the point of attachment of this substituent to the core structure is in the alkyl moiety.

As used herein, "alkyl" means both branched and straight-chain saturated aliphatic hydrocarbon groups having the specified number of carbon atoms. Thus, the term $C_1$-$C_6$ alkyl as used herein includes alkyl groups having from 1 to about 6 carbon atoms. Examples of alkyl groups include, but are not limited to, methyl, ethyl, n-propyl, isopropyl, n-butyl, t-butyl, n-pentyl and sec-pentyl.

As used herein, "alkoxy" means an alkyl group as defined above with the indicated number of carbon atoms attached through an oxygen bridge. Examples of alkoxy groups include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy and 3-methylpentoxy.

As used herein, the term "aryl" means an aromatic group containing only carbon in the aromatic ring or rings. An aryl group may contain 1 to 3 separate, fused, or pendant rings and from 6 to about 18 ring atoms, without heteroatoms as ring members. Examples of aryl groups include, but are not limited to, phenyl, naphthyl, including 1-naphthyl and 2-naphthyl and bi-phenyl. The term "arylalkyl" includes, but is not limited to, benzyl, phenylethyl and piperonyl.

As used herein, "heteroaryl" means a stable 5- to 7-membered monocyclic or 7- to 30-membered bicyclic or tricyclic heterocyclic ring containing at least 1 aromatic ring that contains from 1 to 4, or specifically from 1 to 3, heteroatoms chosen from N, O, S and P with the remaining ring atoms being carbon. When the total number of S, O or P atoms in the heteroaryl group exceeds 1, these heteroatoms are not adjacent to one another. In an embodiment, the total number of S, O and P atoms in the heteroaryl group is not more than 2. In an embodiment the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, S and P to form, for example, a [1,3] dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl and 5,6,7,8-tetrahydroisoquinoline.

As used herein, "cycloalkyl" means a saturated hydrocarbon ring group having only carbon ring atoms and having the specified number of carbon atoms, usually from 3 to about 20 ring carbon atoms, or from 3 to about 7 carbon atoms. Examples of cycloalkyl groups include, but are not limited to, cyclopropyl, cyclobutyl, cyclopentyl and cyclohexyl as well as bridged or caged saturated ring groups such as norborane and adamantane.

The term "heterocycloalkyl" means a saturated cyclic group containing from 1 to about 3 heteroatoms chosen from N, O, S and P with remaining ring atoms being carbon. Heterocycloalkyl groups may have about 3 to about 30 ring atoms, and specifically about 5 to 7 ring atoms. Examples of heterocycloalkyl groups include, but are not limited to, morpholinyl, piperazinyl, piperidinyl and pyrrolidinyl. A nitrogen in a heterocycloalkyl group may optionally be quaternized.

A carbazole compound and an organo-electroluminescent device comprising the carbazole compound will be further described.

A carbazole compound according to an embodiment is represented by Formula 1 below.

Formula 1

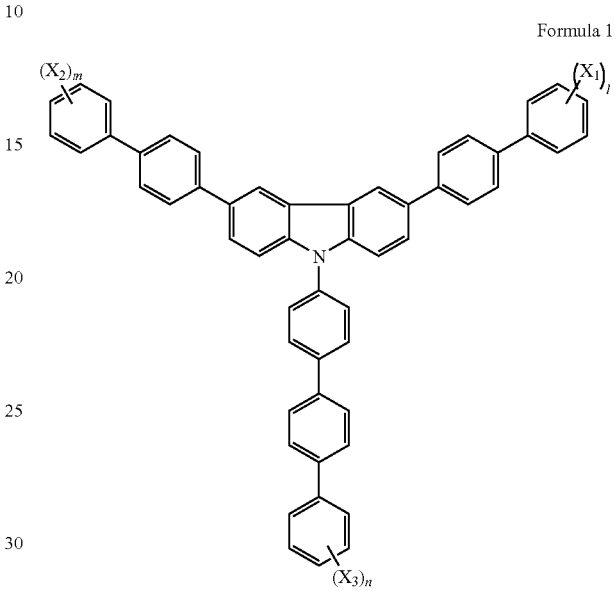

In Formula 1, $X_1$, $X_2$ and $X_3$ are each independently selected from the group consisting of a hydrogen atom, a substituted or unsubstituted $C_1$-$C_{20}$ alkyl group, a substituted or unsubstituted $C_1$-$C_{20}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 0 to 5. It is to be understood that as used herein, "independently selected" means that when a plurality of the $X_1$, $X_2$, and $X_3$ groups are present in the compound, each of the $X_1$, $X_2$, and $X_3$ groups may be the same or different from each other.

In an embodiment, $X_1$, $X_2$ and $X_3$ in Formula 1 are each independently selected from the group consisting of a hydrogen atom, a substituted or unsubstituted $C_1$-$C_{10}$ alkyl group, a substituted or unsubstituted $C_1$-$C_{10}$ alkoxy group, a substituted or unsubstituted $C_6$-$C_{30}$ aryl group, a substituted or unsubstituted $C_6$-$C_{30}$ arylalkyl group, a substituted or unsubstituted $C_2$-$C_{16}$ heteroaryl group, a substituted or unsubstituted $C_3$-$C_{10}$ cycloalkyl group and a substituted or unsubstituted $C_5$-$C_{20}$ heterocycloalkyl group.

In another embodiment, $X_1$, $X_2$ and $X_3$ are each independently selected from the group consisting of a hydrogen atom, an unsubstituted $C_1$-$C_{10}$ alkyl group, an unsubstituted $C_1$-$C_{10}$ alkoxy group, a substituted or unsubstituted $C_6$-$C_{12}$ aryl group, a substituted or unsubstituted $C_2$-$C_5$ heteroaryl group and a substituted or unsubstituted $C_3$-$C_6$ cycloalkyl group.

In an embodiment, the aryl group represented by Formula 1 may be a monovalent group having two or more aromatic rings, which may be bound together so as to be fused with each other.

When the alkyl group, the alkoxy group, the aryl group, the heteroaryl group, the cycloalkyl group or the heterocycloalkyl group are substituted, the substituent may be at least one group selected from the group consisting of —F, —Cl, —Br, —CN, —NO$_2$, —OH, a $C_1$-$C_{20}$ alkyl group that is unsubstituted or substituted with —F, —Cl, —Br, —CN, —NO₂, —OH or a combination thereof, a C₁-C₂₀ alkoxy group that is unsubstituted or substituted with —F, —Cl, —Br, —CN, —NO₂, —OH or a combination thereof, a C₆-C₃₀ aryl group that is unsubstituted or substituted with —F, —Cl, —Br, —CN, —NO₂, —OH or a combination thereof, a C₅-C₃₀ heteroaryl group that is unsubstituted or substituted with —F, —Cl, —Br, —CN, —NO₂, —OH or a combination thereof, a C₅-C₂₀ cycloalkyl group that is unsubstituted or substituted with —F, —Cl, —Br, —CN, —NO₂, —OH or a combination thereof and a C₅-C₃₀ heterocycloalkyl group that is unsubstituted or substituted with —F, —Cl, —Br, —CN, —NO₂, —OH or a combination thereof.

In an embodiment, $X_1$, $X_2$ and $X_3$ are each independently unsubstituted or substituted with at least one group selected from the group consisting of an unsubstituted C₁-C₂₀ alkyl group, an unsubstituted C₁-C₂₀ alkoxy group, an unsubstituted C₆-C₃₀ aryl group, an unsubstituted C₅-C₃₀ heteroaryl group, an unsubstituted C₅-C₂₀ cycloalkyl group and an unsubstituted C₅-C₃₀ heterocycloalkyl group.

In another embodiment, l, m and n are each independently an integer from 1 to 4.

Without wanting to be bound by theory, it is believed that the improved ability of the carbazole compound represented by Formula 1 to form a film by wet coating is due to its improved solubility and amorphous properties. These in turn may be due to the structure of the compound, in which the carbon atoms at the 3- and 6-positions of the carbazole are substituted with biphenyl groups or derivatives thereof and the nitrogen atom at the 9-position of the carbazole is substituted with a triphenyl group or derivative thereof.

The carbazole compound represented by Formula 1 may be one of the compounds represented by Formulae 2 to 11 below.

Formula 2

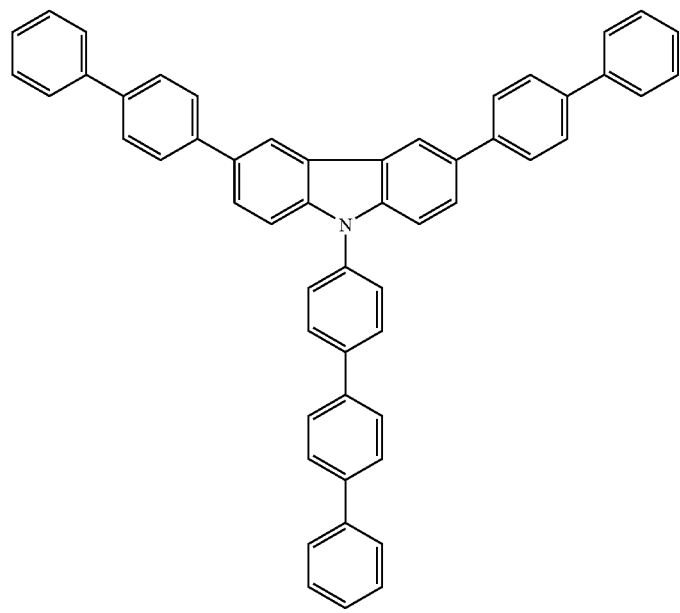

Formula 3

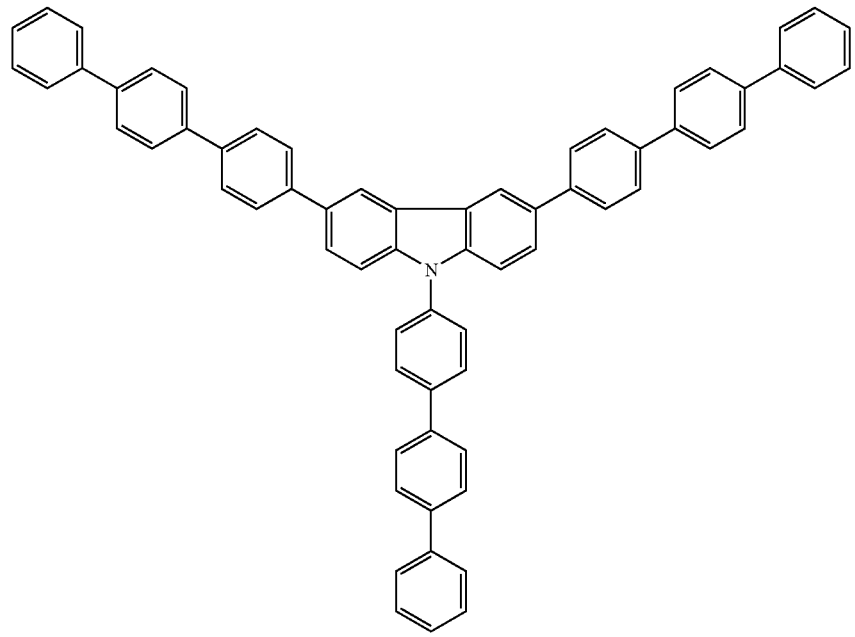

Formula 4
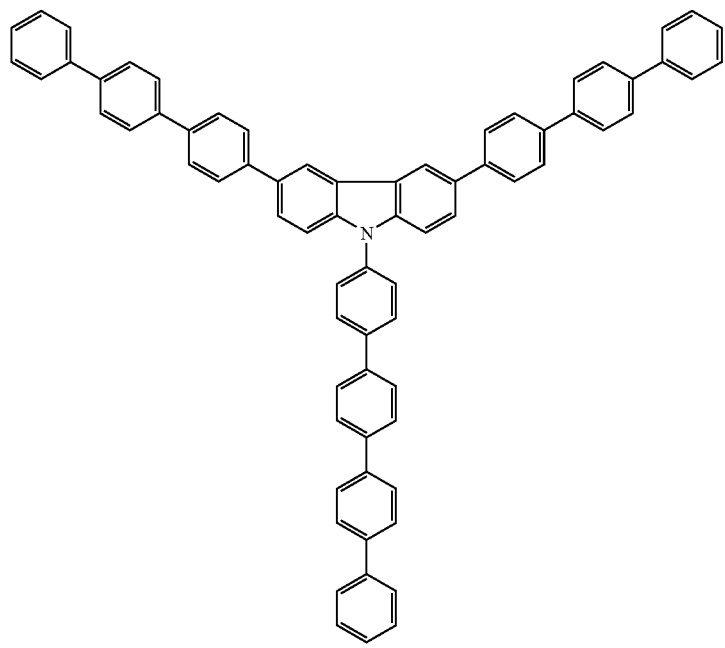
Formula 5
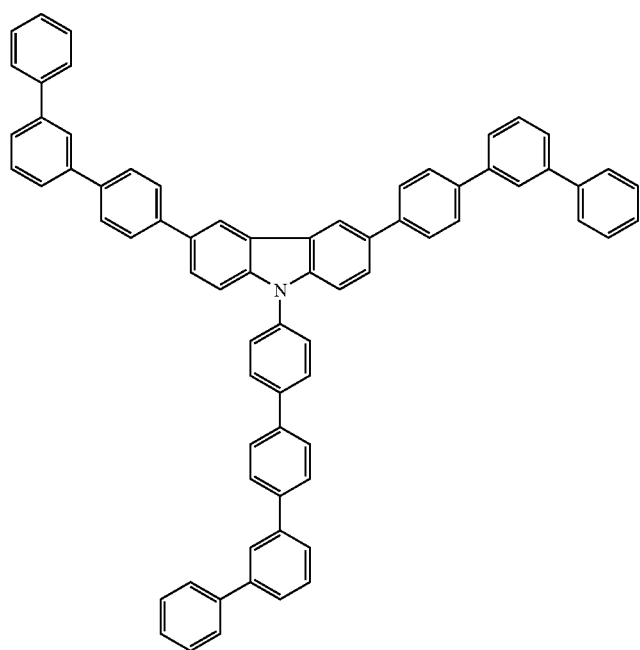

Formula 6
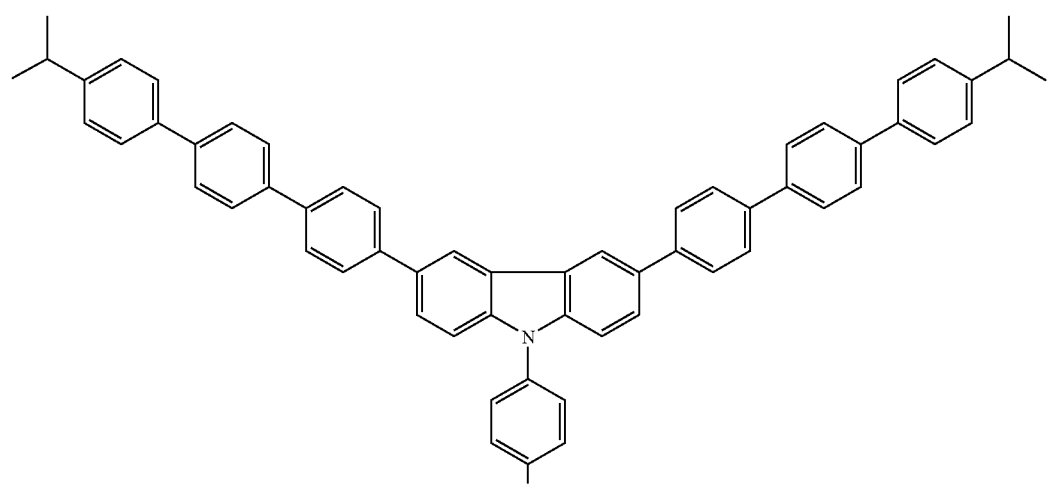
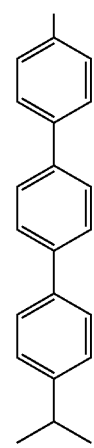
Formula 7
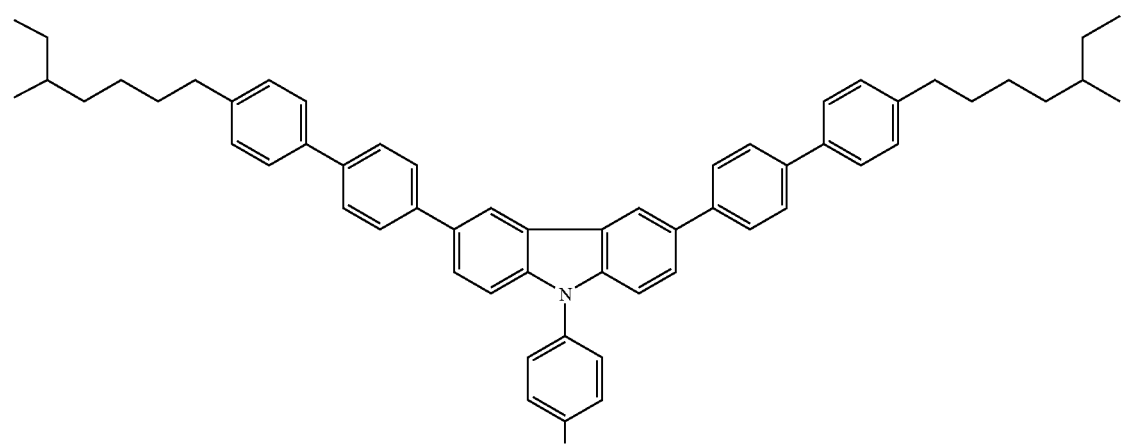

-continued
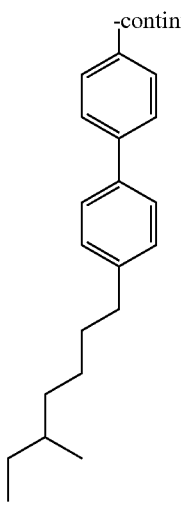
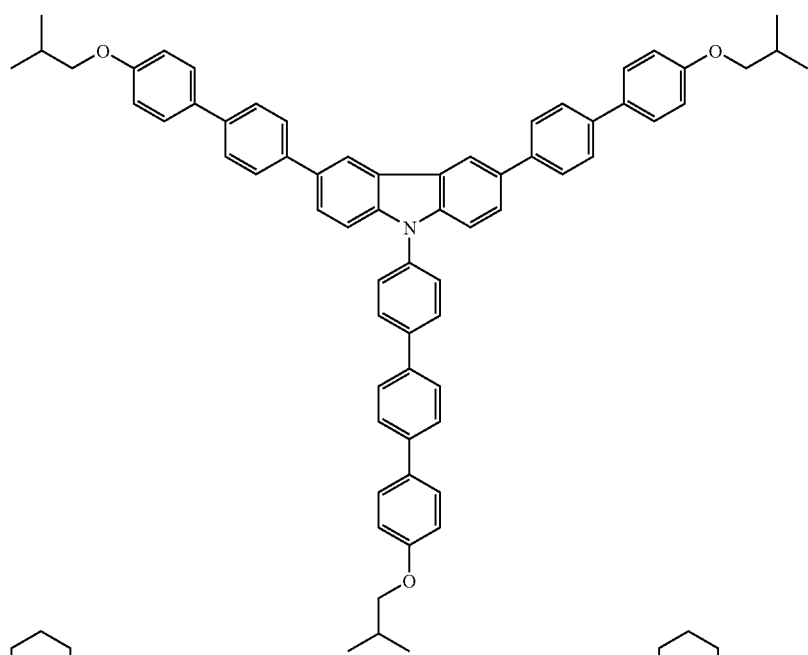
Formula 8
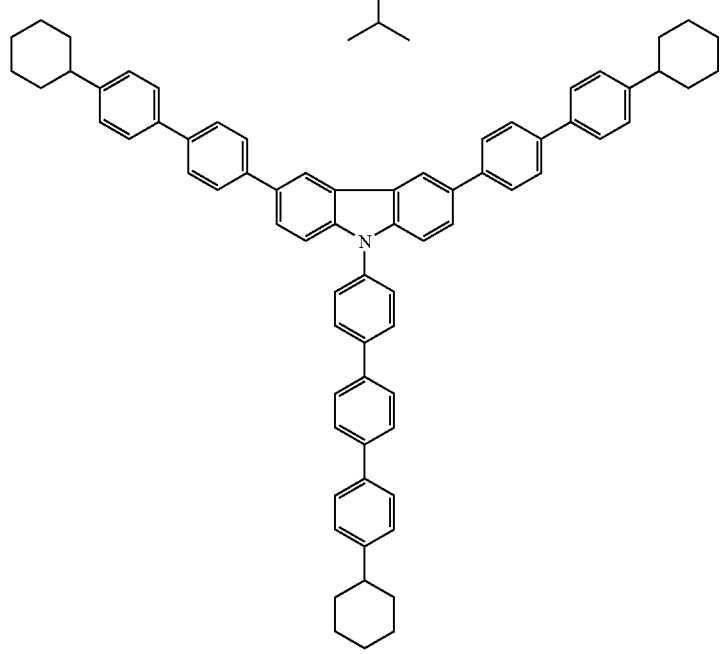
Formula 9

Formula 10
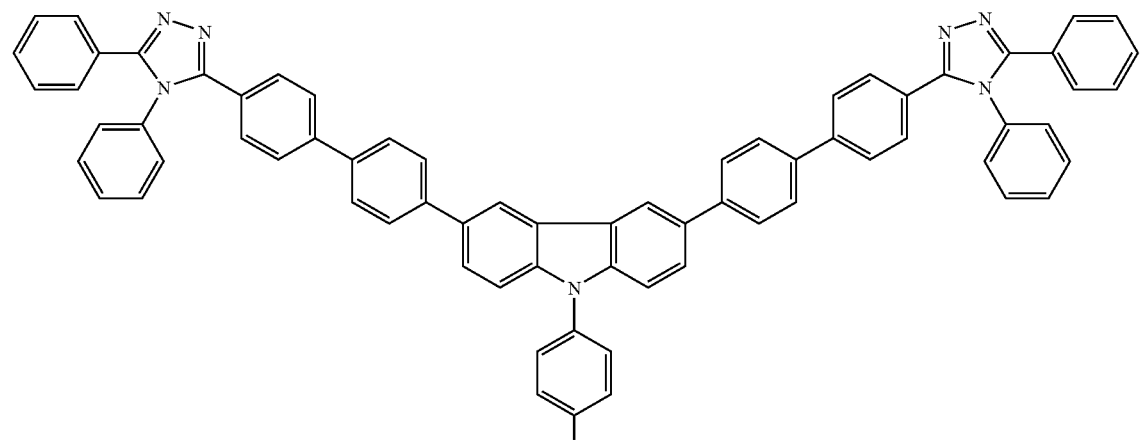
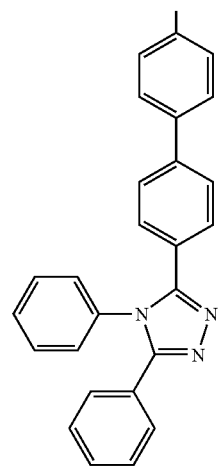
Formula 11
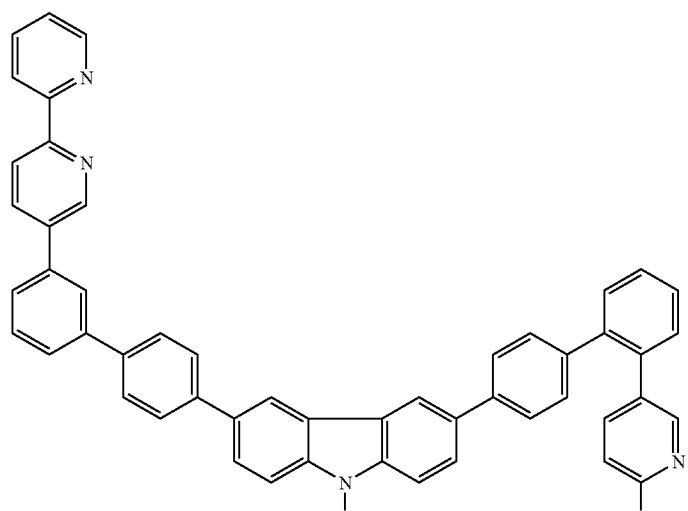

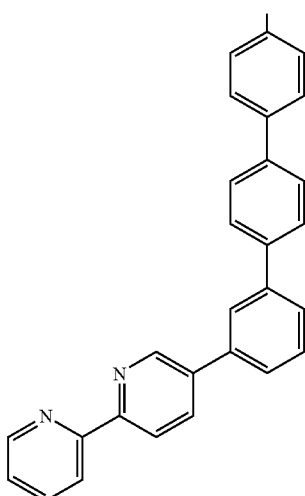
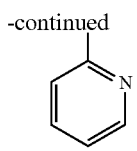

-continued

The carbazole compound represented by Formula 1 may be synthesized using a known method in the art and can be readily synthesized by one of ordinary skill in the art without undue experimentation. An exemplary method of synthesizing the carbazole represented by Formula 1 is shown in the reaction schemes below. For example, 9H-carbazole may be mixed with 1,4-dibromobenzene to obtain 9-(4-bromo-phenyl)-9H-carbazole. The 9-(4-bromo-phenyl)-9H-carbazole may be mixed with N-bromosuccinimide to obtain 3,6-dibromo-9-(4-bromophenyl)-9H-carbazole. Then, the 3,6-dibromo-9-(4-bromophenyl)-9H-carbazole may be mixed with a substituted or unsubstituted 4-biphenyl boronic acid to obtain the carbazole compound.

An organo-electroluminescent device according to another embodiment comprises: a first electrode; a second electrode; and at least one organic layer interposed between the first electrode and the second electrode, wherein the at least one organic layer comprises a carbazole compound represented by Formula 1.

The carbazole compound represented by Formula 1 may be used to form an organic layer, such as an emission layer ("EML"), a hole injection layer ("HIL") or a hole transport layer ("HTL") that can be used in the organo-electroluminescent device.

The organo-electroluminescent device according to an embodiment has excellent luminescence properties such as low driving voltage and high color purity, due to use of the compound represented by Formula 1, which has excellent solubility, thermal stability, and ability to forming a stable organic layer.

The organo-electroluminescent device may have various structures. In an embodiment, the organo-electroluminescent device may comprise at least one organic layer selected from the group consisting of an HIL, an HTL, an EML, a hole blocking layer ("HBL"), an electron blocking layer ("EBL"), an electron transport layer ("ETL") and an electron injection layer ("EIL"), and the organic layer may be interposed between the first electrode and the second electrode. The first electrode may be on a substrate.

Figure 1B:
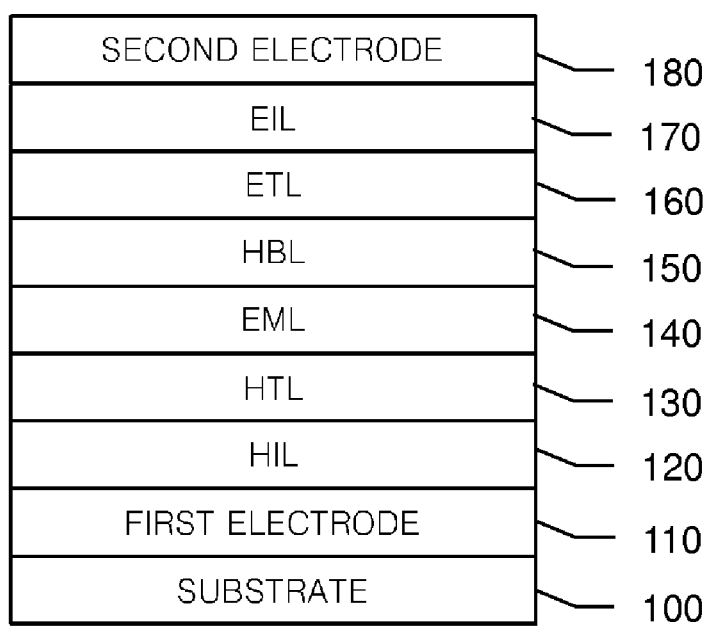

FIGS. 1A and 1B are schematic sectional views illustrating an exemplary embodiment of an organo-electroluminescent device. The organo-electroluminescent device of FIG. 1A has a structure that may be represented as first electrode/HIL/HTL/EML/ETL/EIL/second electrode, and the organo-electroluminescent device of FIG. 1B has a structure that may be represented as first electrode/HIL/HTL/EML/HBL/ETL/EIL/second electrode. Thus the HIL 120 may be on the first electrode 110, the HTL 130 may be on the HIL, the EML 140 may be on the HTL, the ETL 160 may be on the EML, the EIL 170 my be on the ETL and the second electrode 180 may be on the EIL. The first electrode 110 may be disposed on a substrate 100. In another embodiment, the HIL 120 may be on the first electrode, the HTL 130 may be on the HIL, the EML 140 may be on the HTL, the HBL 150 may be on the EML, the ETL 160 may be on the HBL, the EIL 170 may be on the ETL and the second electrode 180 may be on the EIL. In this regard, at least one layer selected from the group consisting of the EML, the HIL and the HTL may include the carbazole compound represented by Formula 1.

Hereinafter, a method of manufacturing the organo-electroluminescent device will be further described. First, a first electrode is disposed (e.g., formed) on a substrate by depositing or sputtering a high work-function material. The first electrode may be an anode. The substrate may be any substrate that is used in organo-electroluminescent devices, and may be a glass substrate, a transparent plastic substrate or the like and may have desirable mechanical strength, thermal stability, transparency, surface smoothness, ease of treatment and may be waterproof. The material that is used to form the first electrode may comprise indium tin oxide ("ITO"), indium zinc oxide ("IZO"), tin oxide ($SnO_2$), zinc oxide (ZnO), or the like or a combination comprising at least one of the foregoing or may be any other transparent material having high conductivity.

Then, a HIL may be disposed (e.g., formed) on the first electrode by vacuum deposition, spin coating, casting, Langmuir-Blodgett ("LB") film deposition or the like.

When the HIL is formed by vacuum deposition, deposition conditions may vary according to a compound that is used to form the HIL and according to the structure and thermal properties of the HIL to be formed. In general, however, conditions for vacuum deposition may include a deposition temperature of about 100 to about 500° C., specifically about 200 to about 400° C., more specifically about 300° C., a pressure of about $10^{-8}$ to about $10^{-3}$ torr, specifically about $10^{-7}$ to about $10^{-4}$ torr, more specifically about $10^{-6}$ to about $10^{-6}$ torr, a deposition speed of about 0.01 to about 100 angstroms per second ("Å/sec"), specifically about 0.1 to about 10 Å/sec, more specifically about 0.5 to about 5 Å/sec and a layer thickness of about 10 angstroms ("A") to about 5 micrometers ("μm"), specifically about 10 nanometers to about 0.5 μm, more specifically about 100 nanometers.

When the HIL is formed by spin coating, coating conditions may vary according to the compound that is used to form the HIL and according to the structure and thermal properties of the HIL to be formed. In general, however, conditions for spin coating may include a coating speed of about 2000 to about 5000 revolutions per minute ("rpm"), specifically about 3000 to about 4000 rpm, more specifically about 3500 rpm and a heat-treatment temperature of about 80° C. to about 200° C., specifically about 100° C. to about 180° C., more specifically about 120° C. to about 160° C. to remove a solvent after coating.

The material that is used to form the HIL may comprise the carbazole compound represented by Formula 1, any organic or organometallic compound used to form the HIL, or a combination thereof. Exemplary materials for the HIL may include, but are not limited to, copper phthalocyanine, 1,3,5-tricarbazolyl benzene, 4,4'-biscarbazolyl biphenyl, polyvinylcarbazole, m-biscarbazolylphenyl, 4,4'-biscarbazolyl-2,2'-dimethyl biphenyl, 4,4',4''-tris(N-carbazolyl)-triphenylamine ("TCTA"), 4,4',4''-tris(3-methylphenylamino)triphenylamine ("m-MTDATA"), 1,3,5-tri(2-carbazolylphenyl)benzene, 1,3,5-tris(2-carbazolyl-5-methoxyphenyl)benzene, bis(4-carbazolylphenyl)silane, N,N'-bis(3-methylphenyl)-N,N'-diphenyl-[1,1-biphenyl]-4,4'diamine ("TPD"), N,N'-di(naphthalene-1-yl)-N,N'-diphenyl benzidine ("α-NPD"), N,N'-diphenyl-N,N'-bis(1-naphthyl)-(1,1'-biphenyl)-4,4'-diamine ("NPB"), poly(9,9-dioctylfluorene-co-N-(4-butylphenyl)diphenylamine) ("TFB"), poly(9,9-dioctylfluorene-co-bis-N,N-phenyl-1,4-phenylenediamine) ("PFB") or the like. In addition, any material known to be useful to form an HIL, which is soluble and is a conductive polymer, such as polyaniline/dodecylbenzenesulfonic acid ("Pani/DBSA"), poly(3,4-ethylenedioxythiophene)/poly(4-styrenesulfonate) ("PEDOT/PSS"), polyaniline/camphor sulfonic acid ("Pani/CSA") or (polyaniline)/poly(4-styrene-sulfonate) ("PANI/PSS") may be used without limitation.

The thickness of the HIL may be about 100 to about 10000 Å, specifically about 300 to about 5000 Å, more specifically about 1000 to about 2000 Å. In an embodiment, the thickness of the HIL may be about 100 to about 1000 Å. If the thickness of the HIL is about 100 to about 10000 Å, a hole injecting capability may be improved and a driving voltage may be reduced.

An HTL may be disposed (e.g., formed) on the HIL by vacuum deposition, spin coating, casting, LB film deposition or the like. When the HTL is formed by vacuum deposition or spin coating, the conditions for deposition and coating may be similar to those for forming the HIL, although conditions for the deposition and coating may vary according to the material that is used to form the HTL.

The material used to form the HTL may be the carbazole compound represented by Formula 1, any known material used to form the HTL or a combination thereof. Exemplary materials for the HTL may include, but are not limited to, copper phthalocyanine, 1,3,5-tricarbazolyl benzene, 4,4'-biscarbazolyl biphenyl, polyvinylcarbazole, m-biscarbazolylphenyl, 4,4'-biscarbazolyl-2,2'-dimethyl biphenyl, TCTA, m-MTDATA, 1,3,5-tri(2-carbazolylphenyl)benzene, 1,3,5-tris(2-carbazolyl-5-methoxyphenyl)benzene, bis(4-carbazolylphenyl)silane, TPD, α-NPD, NPB, TFB and PFB.

The thickness of the HTL may be about 50 to about 1000 Å, specifically about 100 to about 900 Å, more specifically about 200 to about 800 Å. In an embodiment, the thickness of the HTL may be about 100 to about 600 Å. If the thickness of the HTL is about 50 to about 1000 Å, a hole transporting capability may be improved and a driving voltage may be reduced.

An EML may be disposed (e.g., formed) on the HTL by vacuum deposition, spin coating, casting, LB film deposition or the like. When the EML is formed by vacuum deposition or spin coating, the conditions for deposition and coating may be similar to those for the forming of the HIL, although the conditions for the deposition and coating may vary according to the material that is used to form the EML.

The EML may include the carbazole compound represented by Formula 1. The carbazole compound may be used alone or with a fluorescent host or a dopant. For example, the carbazole compound represented by Formula 1 may be used alone as a phosphorescent host, or in combination with 1,3-bis(carbazole-9-yl)benzene ("mCP"), 1,3,5-tris(carbazole-9-yl)benzene ("tCP"), 4,4',4''-tris(carbazole-9-yl)triphenylamine ("TcTa"), 4,4'-bis(carbazole-9-yl)biphenyl ("CBP"), 4,4'-bis(9-carbazolyl)-2,2'-dimethyl-biphenyl ("CBDP"), 4,4'-bis(carbazole-9-yl)-9,9-dimethyl-fluorene ("DMFL-CBP"), 4,4'-bis(carbazole-9-yl)-9,9-bis(9-phenyl-9H-carbazole)fluorene ("FL-4CBP"), 4,4'-bis(carbazole-9-yl)-9,9-di-tolyl-fluorene ("DPFL-CBP"), 9,9-bis(9-phenyl-9H-carbazole)fluorene ("FL-2CBP"), or the like or a combination thereof. A phosphorescent dopant used in the EML may be an organometallic compound including an organometallic compound comprising at least one element selected from the group consisting of Ir, Pt, Os, Ti, Zr, Hf, Eu, Tb and Tm. Examples of the phosphorescent dopant include a red phosphorescent dopant such as (btp)2Ir(acac), wherein "btp" is 2-(2'-benzo[4,5-α]thienyl)pyridinato and "acac" is acetylacetonate; (piq)3Ir, wherein "piq" is 1-phenylisoquinolinato; (piq)2Ir(acac); Pt(II) octaethylporphine ("PtOEP") and RD 61, which may be obtained from Universal Display Technology Company Limited ("UDC Co."); a green phosphorescent dopant such as Ir(PPy)$_3$, wherein "PPy" is 2-phenylpyridine and a blue phosphorescent dopant such as F$_2$Irpic. In an embodiment, another metal compound may also be used without limitation.

If the carbazole compound represented by Formula 1 is used as a sole host in the EML, the concentration of the dopant may be about 0.01 to about 15 parts by weight, specifically about 0.1 to about 10 parts by weight, more specifically about 1 to about 5 parts by weight based on 100 parts by weight of the carbazole compound represented by Formula 1. If the carbazole compound represented by Formula 1 is not used as a sole host in the EML, the concentration of the carbazole compound may be about 30 to about 99 weight percent ("wt %"), specifically 40 to about 90 wt %, more specifically 50 to about 80 wt %, based on the total weight of the host.

The thickness of the EML may be about 100 to about 1000 Å, specifically about 200 to about 900 Å, more specifically about 300 to about 800 Å. In another embodiment, the thickness of the EML may be about 200 to about 600 Å. If the thickness of the EML is about 100 to about 1000 Å, a light-emitting capability may be improved, and a driving voltage may be reduced.

If the phosphorescent dopant is used with the carbazole compound represented by Formula 1 in the EML, an HBL may be disposed on the EML, e.g., formed by deposition, spin coating, casting, LB film deposition or the like. Without wanting to be bound by theory, it is believed that disposing the HBL on the EML may prevent diffusion of triplet excitons or holes into an ETL. When the HBL is formed by vacuum deposition or spin coating, the conditions for deposition and coating may be similar to those for the forming of the HIL, although conditions for the deposition and coating may vary according to the material that is used to form the HBL. The material that is used to form the HBL may be an oxadiazole derivative, a triazole derivative, a phenanthroline derivative, 2,9-dimethyl-4,7-diphenyl-1,10-phenanthroline ("BCP"), an aluminum complex, or the like or a combination thereof, which is known in the art.

The thickness of the HBL may be about 50 to about 1000 Å, specifically about 100 to about 900 Å, more specifically about 200 to about 800 Å. In an embodiment, the thickness of the HBL may be about 100 to about 300 Å. If the thickness of the HBL is about 50 to about 1000 Å, a hole blocking capability may be improved, and a driving voltage may be reduced.

An ETL may be disposed (e.g., formed) on the EML or the HBL, if the HBL is present, by vacuum deposition, spin coating, casting, LB film deposition or the like. When the ETL is formed by vacuum deposition or spin coating, the conditions for deposition and coating may be similar to those for the forming of the HIL, although conditions for the deposition and coating may vary according to the material that is used to form the ETL. The ETL comprises a material that facilitates transfer of electrons injected from a second electrode, wherein the second electrode may be a cathode. The material that is used to form the ETL may comprise an oxazole compound, an isoxazole compound, a triazole compound, an isothiazole compound, an oxadiazole compound, a thiadiazole compound, a perylene compound, such as the perylene compound having the structure represented by Formula 12 below, or the like or a combination thereof.

Formula 12

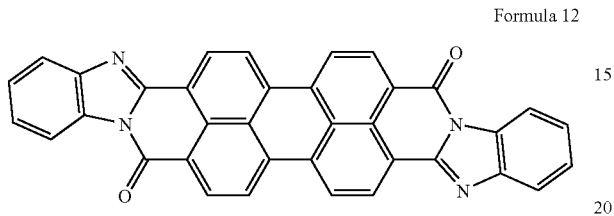

The ETL may also comprise an aluminum complex (e.g., a tris(8-quinolinolato)-aluminum ("$Alq_3$") compound having the structure represented by Formula 13, an aluminum(III)bis (2-methyl-8-quninolinato)-4-phenylphenolate ("BAIq") compound having the structure represented by Formula 14, an aluminum(III)bis(2-methyl-8-quninolinato)-triphenylsilanyloxy ("SAlq") compound having the structure represented by Formula 15, a tris(4-methyl-8-quinolinolato)aluminum ("$Almq_3$") compound having the structure represented by Formula 16, a gallium complex (e.g., the compound represented by Formula 17 ("Gaq'2OPiv"), the compound represented by Formula 18 ("Gaq'2OAc") or the compound represented by Formula 19 ("2(Gaq'2)")) or a bis(10-hydroxybenzo[h]quinolinatoberyllium ("Bebq2") compound having the structure represented by Formula 20.

In an embodiment, any known material may be used to form the ETL.

Formula 13

$Alq_3$

Formula 14

BAlq

Formula 15

SAlq

Formula 16

$Almq_3$

Formula 17

Gaq'2OPiv

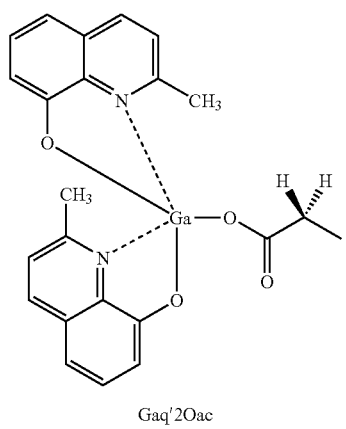

Gaq'2Oac

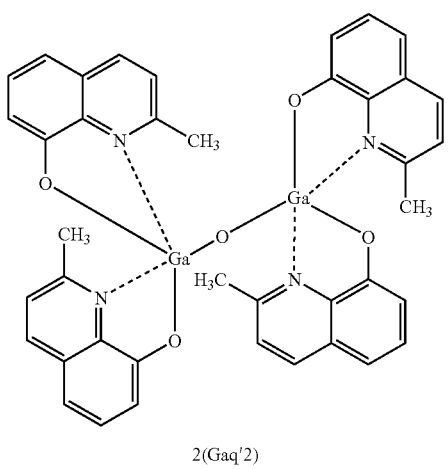

2(Gaq'2)

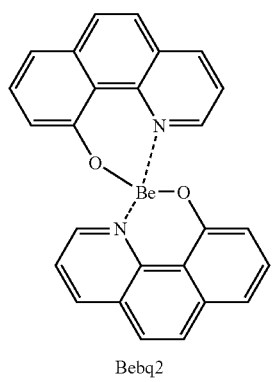

Bebq2

The thickness of the ETL may be about 100 to about 1000 Å, specifically about 200 to about 900 Å, more specifically about 300 to about 800 Å. In an embodiment, the thickness of the ETL may be about 200 to about 500 Å. If the thickness of the ETL is about 100 to about 1000 Å, an electron transporting capability may be improved and a driving voltage may be reduced.

An EIL, which comprises a material allowing easy injection of electrons from a second electrode, may be disposed on the ETL, e.g., formed by vacuum deposition, spin coating, casting, LB film deposition or the like. When the EIL is formed by vacuum deposition or spin coating, the conditions for deposition and coating may be similar to those for the forming of the HIL, although conditions for the deposition and coating may vary according to the material that is used to form the EIL.

The material that is used to form the EIL may comprise LiF, NaCl, CsF, $Li_2O$, BaO, or the like or a combination thereof, which is known in the art.

The thickness of the EIL may be about 1 to about 100 Å, specifically about 5 to about 90 Å, more specifically about 10 to about 80 Å. In an embodiment, the thickness of the EIL may be about 5 to about 50 Å. If the thickness of the EIL is about 1 to about 100 Å, an electron injecting capability may be improved, and a driving voltage may be reduced.

Finally, a second electrode may be disposed on the EIL, e.g., formed on the EIL by vacuum deposition, sputtering or the like. The second electrode may be used as a cathode. The second electrode may be formed from a low work-function metal, an alloy, an electrically conductive compound, or the like or a combination thereof. In particular, the metal may be lithium (Li), magnesium (Mg), aluminum (Al), an aluminum-lithium alloy ("Al—Li"), calcium (Ca), a magnesium-indium alloy ("Mg—In"), a magnesium-silver alloy ("Mg—Ag"), or the like or a combination thereof. In addition, a transparent cathode comprising ITO, IZO or the like may be used to produce a top emission type luminescent device.

Hereinafter, one or more embodiments will be further described in detail with reference to the following examples. However, these examples are not intended to limit the purpose and scope of the embodiments.

Synthesis Example 1

Preparation of Compound Represented by Formula 2

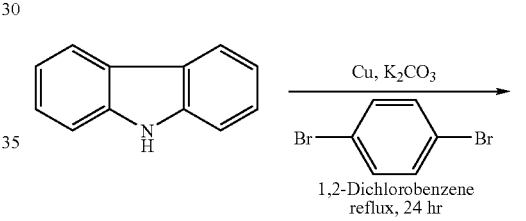

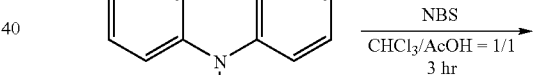

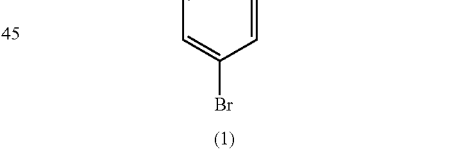

-continued

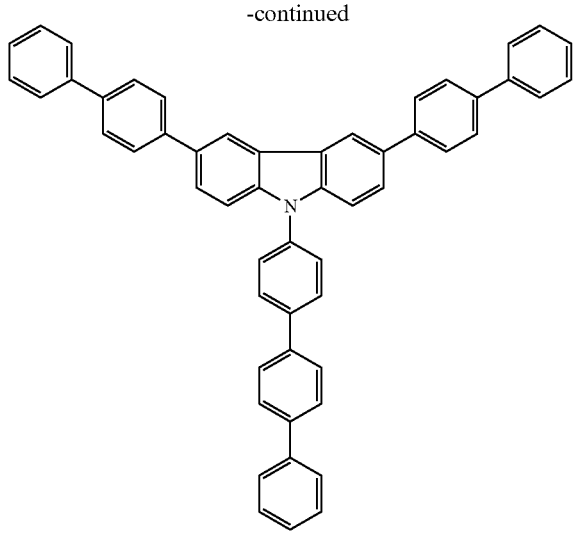

Preparation of Compound 1

A 7 gram (g) (41.9 millimole, mmol) quantity of 9H-carbazole, 25.6 g (100 mmol) of 1,4-dibromobenzene, 0.3 g (4.5 mmol) of copper and 20 g (146 mmol) of potassium carbonate were dissolved in 170 milliliters (ml) of 1,2-dichlorobenzene, and the solution was refluxed for 24 hours. The resulting mixture was treated under reduced pressure to remove 1,2-dichlorobenzene, dissolved in ethyl acetate and washed several times with water. Then, the solvent was removed and the resulting material was dissolved in a small amount of ethyl acetate and filtered to obtain a pale yellow solid intermediate of Compound 1 (10 g, 75%) having the following properties:

$^1$H NMR (300 MHz, $CD_2Cl_2$, δ): 8.21 (d, J=7.5 Hz, 2H), 7.77-7.81 (m, 2H), 7.42-7.53 (m, 6H), 7.32-7.38 (m, 2H). $^{13}$C NMR (300 MHz, $CD_2Cl_2$, δ): 141.2, 137.3, 133.6, 129.2, 126.6, 124.0, 121.3, 120.8, 120.7, 110.1.

Preparation of Compound 2

A 10 g (31 mmol) amount of Compound 1 [9-(4-bromophenyl)-9H-carbazole] was dissolved in 90 ml of chloroform, and 90 ml of acetic acid was added thereto. A 11.6 g (65 mmol) amount of N-bromosuccinimide was added thereto at 0° C. The temperature was increased to room temperature and the maintained for 10 hours. Then, the resulting mixture was filtered. The solid was dissolved in a small amount of toluene and the resulting material was left at 0° C. for 3 days to obtain a white needle-shaped solid intermediate of Compound 2 (9.1 g, 61%) having the following properties:

$^1$H NMR (300 MHz, $CD_2Cl_2$, δ): 8.21 (d, J=1.8 Hz, 2H), 7.73-7.78 (m, 2H), 7.54 (d, J=1.8 Hz, 1H), 7.51 (d, J=1.8 Hz, 1H), 7.38-7.43 (m, 2H), 7.26 (d, J=8.7 Hz, 2H). $^{13}$C NMR (300 MHz, $CD_2Cl_2$, δ): 140.2, 136.4, 133.9, 130.0, 129.1, 124.6, 123.7, 122.1, 113.7, 112.0.

Preparation of Compound Represented by Formula 2

A 1.00 g (2.10 mmol) amount of Compound 2 [3,6-dibromo-9-(4-bromophenyl)-9H-carbazole] was dissolved in 150 ml of toluene. A 0.36 g (0.31 mmol) amount of $Pd(PPh_3)_4$, 12 ml of 2 molar (M) $K_2CO_3$, and 1.37 g (6.92 mmol) of 4-biphenylboronic acid were added thereto. The mixture was treated for 48 hours while increasing the temperature and refluxing. The resulting mixture was treated under reduced pressure to remove the solvent and purified using silica gel column chromatography to obtain a compound represented by Formula 2 (0.91 g, yield: 62%) having the following properties:

$^1$H NMR (300 MHz, $CD_2Cl_2$, δ): 8.57 (d, J=1.2 Hz, 2H), 7.98-8.01 (m, 2H), 7.85-7.92 (m, 7H), 7.78-7.83 (m, 9H), 7.73-7.76 (m, 6H), 7.67 (d, J=8.7 Hz, 2H), 7.49-7.54 (m, 6H), 7.41-7.43 (m, 3H). $^{13}$C NMR (300 MHz, $CD_2Cl_2$, δ): 141.4, 141.2, 141.0, 139.9, 133.5, 129.5, 129.4, 129.0, 128.1, 128.0, 127.8, 127.7, 127.5, 127.4, 126.1, 124.7, 119.2, 110.9.

Synthesis Example 2

Preparation of Compound Represented by Formula 4

A compound represented by Formula 4 was prepared in the same manner as in Synthesis Example 1, except that 6.92 mmol of 4-terphenylboronic acid was used instead of 4-biphenylboronic acid.

Synthesis Example 3

Preparation of Compound Represented by Formula 8

A compound represented by Formula 8 was prepared in the same manner as in Synthesis Example 1, except that 6.92 mmol of 4-isobutoxy-4'-biphenylboronic acid was used instead of 4-biphenylboronic acid.

Evaluation Example

Evaluation of Optical Properties

Luminescence properties of the compounds as a solution and as a film were measured using photoluminescence ("PL") spectra.

To evaluate the optical properties of the compounds in solution, the compounds prepared according to Synthesis Examples 1 to 3 were diluted in toluene to a concentration of 10 millimolar (mM). The PL spectrum of the diluted compounds was measured using an ISC PC1 spectrofluorometer equipped with a Xenon lamp at room temperature (298 K) and at a low temperature (77 K). In addition, to evaluate the optical properties of the compounds as a film, a quartz substrate was washed with acetone and pure water. Then, the compounds prepared according to Synthesis Examples 1 to 3 were spin coated on the quartz substrate and heat treated at 110° C. for 30 minutes to form a film having a thickness of 1000 Å. The PL spectrum of the film was measured. The results are shown in Table 1 below.

TABLE 1

|  | Solution ($\lambda_{max}$) (nm) at room temperature (298 K) | Solution ($\lambda_{max}$) (nm) at low temperature (77 K) | Film ($\lambda_{max}$) (nm) at room temperature (298 K) |
| --- | --- | --- | --- |
| Formula 2 | 393 | 495 | 402 |
| Formula 4 | 413 | 521 | 419 |
| Formula 8 | 395 | 503 | 407 |

As shown in Table 1, the carbazole compound according to an embodiment has a PL spectrum such that it is useful for and may be used in an organo-electroluminescent device.

Examples 1 to 9

Performance as EML Material

An organo-electroluminescent device having the structure anode/HIL/HTL/EML/ETL/EIL/cathode was manufactured using the compounds represented by Formulas 2, 4 and 8, prepared according to Synthesis Examples 1 to 3, respectively, as hosts of the EML and (btp)2Ir(acac), wherein "btp" is 2-(2'-benzo[4,5-α]thienyl)pyridinato and "acac" is acetylacetonate; (piq)3Ir, wherein "piq" is 1-phenylisoquinolinato; and (piq)2Ir(acac) as dopants of the EML. Thus the organo-electroluminescent device had the structure: ITO (100 nm)/MoO$_3$ (10 nm)/NPB (50 nm)/compounds represented by Formula 2, 4, or 8 and (btp)2Ir(acac), (piq)3Ir, or (piq)2Ir(acac) (8% by weight) (30 mm)/Bebq2 (40 nm)/LiF (0.5 nm)/Al (100 nm).

An ITO glass substrate having an ITO thickness of 1000 Å and surface resistivity of 15 Ω/cm$^2$ was cut to a size of 50 mm×50 mm×0.7 mm, ultrasonically washed with acetone, isopropyl alcohol and pure water for 15 minutes, respectively, and washed with UV ozone for 30 minutes. MoO$_3$ and NPB were respectively vacuum deposited on the substrate to a thickness of 10 nm and 50 nm. Each of the compounds represented by Formulas 2, 4, and 8 prepared according to Synthesis Examples 1 to 3, respectively, and each of the phosphorescent dopant compounds (8% by weight) were vacuum deposited to form an EML. Then, Bebq2 was vacuum deposited on the EML to a thickness of 40 nm to form an ETL. LiF was vacuum deposited on the ETL to a thickness of 0.5 nm to form an EIL, and Al was vacuum deposited to a thickness of 100 nm on the EIL to form a cathode. As a result, an organo-electroluminescent device as illustrated in FIG. 1A was manufactured. The electroluminescence properties of the organo-electroluminescent device are shown in Table 2 below.

factured using the compounds represented by Formulae 2, 4, and 8, prepared according to Synthesis Examples 1 to 3, respectively, as hosts of the EML, and (btp)2Ir(acac), (piq)3Ir, and (piq)2Ir(acac) as dopants of the EML. Thus the organo-electroluminescent device had the structure: ITO (100 nm)/MoO$_3$ (10 nm)/NPB (50 nm)/compounds represented by Formula 2, 4, or 8 and (btp)2Ir(acac), (piq)3Ir or (piq)2Ir(acac) (8% by weight)(30 mm)/BCP (10 nm)/Bebq2 (40 nm)/LiF (0.5 nm)/Al (100 nm).

An ITO glass substrate having an ITO thickness of 1000 Å and surface resistivity of 15 Ω/cm$^2$ was cut to a size of 50 mm×50 mm×0.7 mm, ultrasonically washed with acetone, isopropyl alcohol and pure water for 15 minutes, respectively, and washed with UV ozone for 30 minutes. MoO$_3$ and NPB were respectively vacuum deposited on the substrate to a thickness of 10 nm and 50 nm. Each of the compounds represented by Formulae 2, 4, and 8 prepared according to Synthesis Examples 1 to 3, respectively, and each of the phosphorescent dopant compounds (8% by weight) were vacuum deposited to form an EML. Then, BCP was vacuum deposited on the EML to a thickness of 10 nm to form a HBL, and Bebq2 was vacuum deposited on the HBL to a thickness of 40 nm to form an ETL. LiF was vacuum deposited on the ETL to a

TABLE 2

| | | | Electroluminescence (EL) properties | | |
|---|---|---|---|---|---|
| | Host | Dopant | Maximum EL wavelength (λmax) | External Quantum Efficiency (%) | Efficiency at current density of 3 mA/cm$^2$ (cd/A) | Driving voltage (V) |
| Example 1 | Formula 2 | (btp)2Ir(acac) | 624 | 9.8 | 9.5 | 3.3 |
| Example 2 | | (piq)3Ir | 625 | 10.5 | 9.7 | 3.2 |
| Example 3 | | (piq)2Ir(acac) | 623 | 14.3 | 12.1 | 2.9 |
| Example 4 | Formula 4 | (btp)2Ir(acac) | 624 | 8.9 | 9.5 | 3.3 |
| Example 5 | | (piq)3Ir | 625 | 10.1 | 9.8 | 3.2 |
| Example 6 | | (piq)2Ir(acac) | 625 | 12.3 | 11.2 | 2.9 |
| Example 7 | Formula 8 | (btp)2Ir(acac) | 625 | 9.1 | 9.6 | 3.4 |
| Example 8 | | (piq)3Ir | 623 | 9.9 | 9.8 | 3.3 |
| Example 9 | | (piq)2Ir(acac) | 625 | 13.4 | 11.3 | 3.0 |

Examples 10 to 18

Performance as EML Material

An organo-electroluminescent device having the structure anode/HIL/HTL/EML/HBL/ETL/EIL/cathode was manuthickness of 0.5 nm to form an EIL, and Al was vacuum deposited on the EIL to a thickness of 100 nm to form a cathode. As a result, an organo-electroluminescent device as illustrated in FIG. 1B was manufactured. The electroluminescent ("EL") properties of the organo-electroluminescent device are shown in Table 3 below.

TABLE 3

|  | Host | Dopant | EL properties | | | |
|---|---|---|---|---|---|---|
|  |  |  | Maximum EL wavelength (λmax) | External Quantum Efficiency (%) | Efficiency at current density of 3 mA/cm$^2$ (cd/A) | Driving voltage (V) |
| Example 10 | Formula 2 | (btp)2Ir(acac) | 624 | 13.8 | 10.8 | 3.2 |
| Example 11 |  | (piq)3Ir | 625 | 11.8 | 10.9 | 3.2 |
| Example 12 |  | (piq)2Ir(acac) | 623 | 19.3 | 16.4 | 2.9 |
| Example 13 | Formula 4 | (btp)2Ir(acac) | 624 | 11.3 | 10.2 | 3.3 |
| Example 14 |  | (piq)3Ir | 625 | 10.9 | 10.5 | 3.2 |
| Example 15 |  | (piq)2Ir(acac) | 625 | 17.2 | 13.2 | 3.0 |
| Example 16 | Formula 8 | (btp)2Ir(acac) | 625 | 11.7 | 10.6 | 3.4 |
| Example 17 |  | (piq)3Ir | 623 | 10.3 | 10.3 | 3.4 |
| Example 18 |  | (piq)2Ir(acac) | 625 | 15.4 | 12.3 | 3.2 |

As shown in Tables 2 and 3, the organo-electroluminescent device manufactured according to an embodiment has high luminescence efficiency at a low driving voltage.

Examples 19 to 27

Performance as HTL Material

An organo-electroluminescent device having the structure anode/HIL/HTL/EML/ETL/EIL/cathode was manufactured using the compounds represented by Formulas 2, 4, and 8, prepared according to Synthesis Examples 1 to 3, respectively, as an HTL and hosts of an EML, and (btp)2Ir(acac), (piq)3Ir and (piq)2Ir(acac) as dopants of the EML. Thus the organo-electroluminescent device had the structure: ITO (100 nm)/MoO$_3$ (10 nm)/compounds represented by Formula 2, 4, or 8 (50 nm)/compounds represented by Formula 2, 4, or 8 and (btp)2Ir(acac), (piq)2Ir or (piq)2Ir(acac) (8% by weight)(30 mm)/Bebq2 (40 nm)/LiF (0.5 nm)/Al (100 nm).

As a result, an organo-electroluminescent device illustrated in FIG. 1A was manufactured. The electroluminescence properties of the organo-electroluminescent device are shown in Table 4 below.

TABLE 4

|  | Host and HTL | Dopant | EL properties | | | |
|---|---|---|---|---|---|---|
|  |  |  | Maximum EL wavelength (λmax) | External Quantum Efficiency (%) | Efficiency at current density of 3 mA/cm$^2$ (cd/A) | Driving voltage (V) |
| Example 19 | Formula 2 | (btp)2Ir(acac) | 624 | 10.1 | 10.6 | 3.1 |
| Example 20 |  | (piq)3Ir | 625 | 10.8 | 11.5 | 3.0 |
| Example 21 |  | (piq)2Ir(acac) | 623 | 16.4 | 14.1 | 2.8 |
| Example 22 | Formula 4 | (btp)2Ir(acac) | 625 | 9.8 | 10.1 | 3.0 |
| Example 23 |  | (piq)3Ir | 624 | 10.2 | 10.9 | 3.0 |
| Example 24 |  | (piq)2Ir(acac) | 625 | 15.2 | 14.2 | 2.9 |
| Example 25 | Formula 8 | (btp)2Ir(acac) | 625 | 9.9 | 10.3 | 3.1 |
| Example 26 |  | (piq)3Ir | 624 | 10.1 | 10.7 | 3.0 |
| Example 27 |  | (piq)2Ir(acac) | 625 | 15.4 | 13.3 | 2.9 |

As shown in Table 4, the organo-electroluminescent device according to an embodiment in which the carbazole compound is used as a material for the HTL and the EML has high luminescence efficiency at a low driving voltage.

As disclosed above, the organo-electroluminescent device comprising the carbazole compound of Formula 1 in an organic layer has advantageous and desirable electroluminescence properties.

The carbazole compound has excellent thermal stability, and the organo-electroluminescent device including the carbazole compound has excellent luminescence efficiency, high color purity and a low driving voltage.

It is understood that the exemplary embodiments described herein are to be considered in a descriptive sense only and not for purposes of limitation. Descriptions of features, aspects or advantages within each embodiment are to be considered as available for other similar features, aspects or advantages in other embodiments.

What is claimed is:

1. A carbazole compound represented by Formula 1:

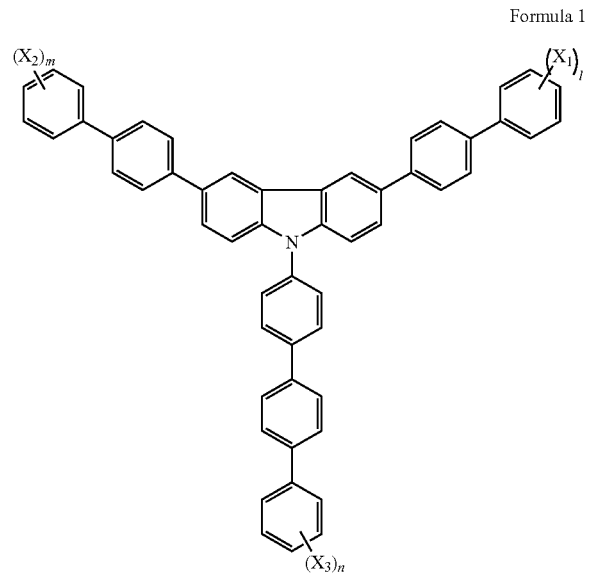

Formula 1 wherein $X_1$, $X_2$ and $X_3$ are each independently selected from the group consisting of a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 1 to 5.

2. The carbazole compound of claim 1, wherein $X_1$, $X_2$ and $X_3$ are each independently unsubstituted or substituted with at least one group selected from the group consisting of —F, —Cl, —Br, —CN, —NO$_2$, —OH, a $C_1$-$C_{20}$ alkyl group that is unsubstituted or substituted with —F, —Cl, —Br, —CN, —NO$_2$, —OH or a combination thereof, a $C_1$-$C_{20}$ alkoxy group that is unsubstituted or substituted with —F, —Cl, —Br, —CN, —NO$_2$, —OH or a combination thereof, a $C_6$-$C_{30}$ aryl group that is unsubstituted or substituted with —F, —Cl, —Br, —CN, —NO$_2$, —OH or a combination thereof, a $C_5$-$C_{30}$ heteroaryl group that is unsubstituted or substituted with —F, —Cl, —Br, —CN, —NO$_2$, —OH or a combination thereof, a $C_5$-$C_{20}$ cycloalkyl group that is unsubstituted or substituted with —F, —Cl, —Br, —CN, —NO$_2$, —OH or a combination thereof and a $C_5$-$C_{30}$ heterocycloalkyl group that is unsubstituted or substituted with —F, —Cl, —Br, —CN, —NO$_2$, —OH or a combination thereof.

3. The carbazole of claim 1, wherein $X_1$, $X_2$ and $X_3$ are each independently selected from the group consisting of a substituted or unsubstituted $C_6$-$C_{30}$ aryl group, a substituted or unsubstituted $C_6$-$C_{30}$ arylalkyl group, a substituted or unsubstituted $C_2$-$C_{16}$ heteroaryl group, a substituted or unsubstituted $C_3$-$C_{10}$ cycloalkyl group and a substituted or unsubstituted $C_5$-$C_{20}$ heterocycloalkyl group.

4. The carbazole of claim 1, wherein $X_1$, $X_2$ and $X_3$ are each independently selected from the group consisting of a substituted or unsubstituted $C_6$-$C_{12}$ aryl group, a substituted or unsubstituted $C_2$-$C_5$ heteroaryl group and a substituted or unsubstituted $C_3$-$C_6$ cycloalkyl group.

5. The carbazole of claim 1, wherein $X_1$, $X_2$ and $X_3$ are each independently unsubstituted or substituted with at least one group selected from the group consisting of an unsubstituted $C_1$-$C_{20}$ alkyl group, an unsubstituted $C_1$-$C_{20}$ alkoxy group, an unsubstituted $C_6$-$C_{30}$ aryl group, an unsubstituted $C_5$-$C_{30}$ heteroaryl group, an unsubstituted $C_5$-$C_{20}$ cycloalkyl group and an unsubstituted $C_5$-$C_{30}$ heterocycloalkyl group.

6. The carbazole of claim 1, wherein l, m and n are each independently an integer from 1 to 4.

7. The carbazole compound of claim 1, wherein the compound is selected from the group consisting of the compounds represented by Formulas 4 to 6 and 9 to 11:

Formula 4
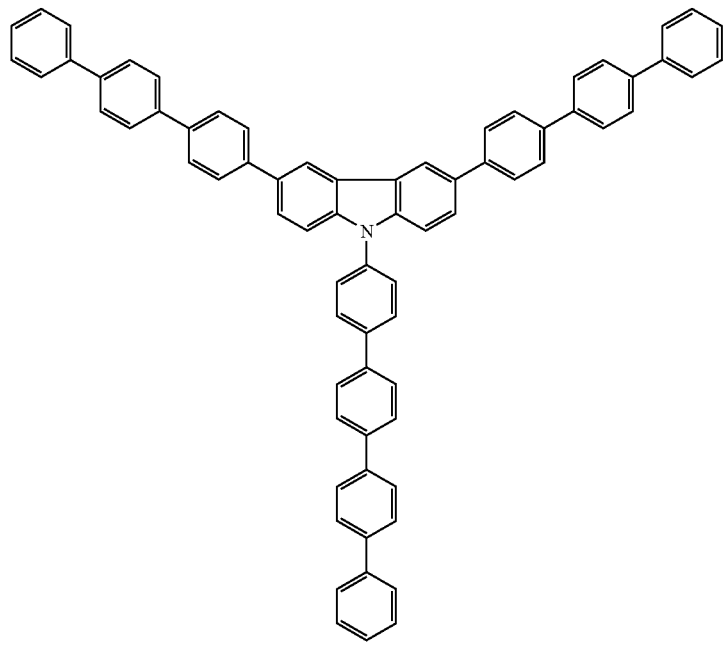
Formula 5
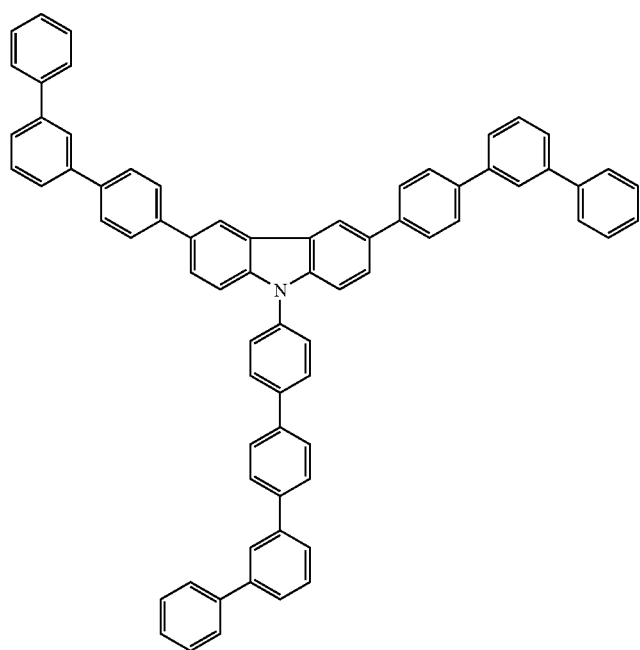

-continued
Formula 6
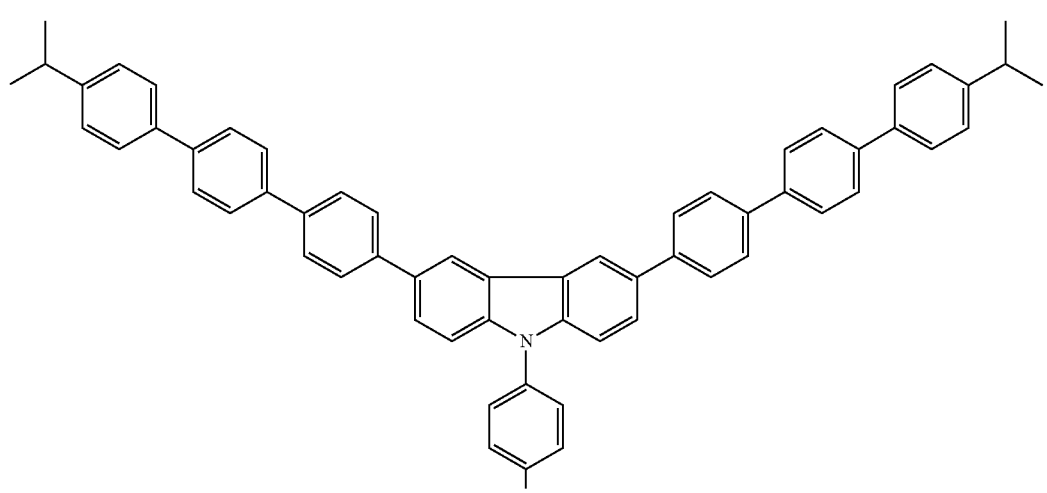
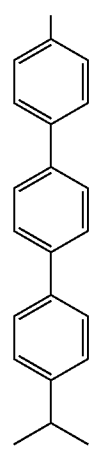
Formula 9
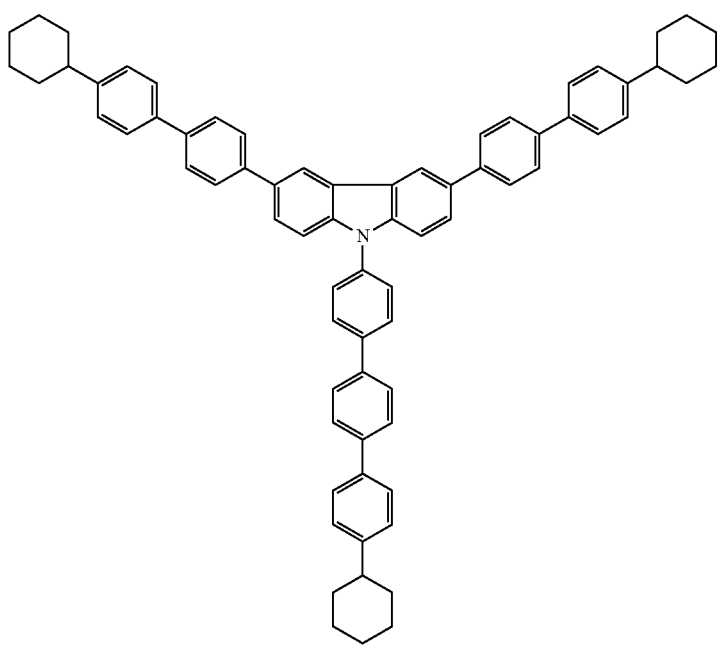

-continued
Formula 10
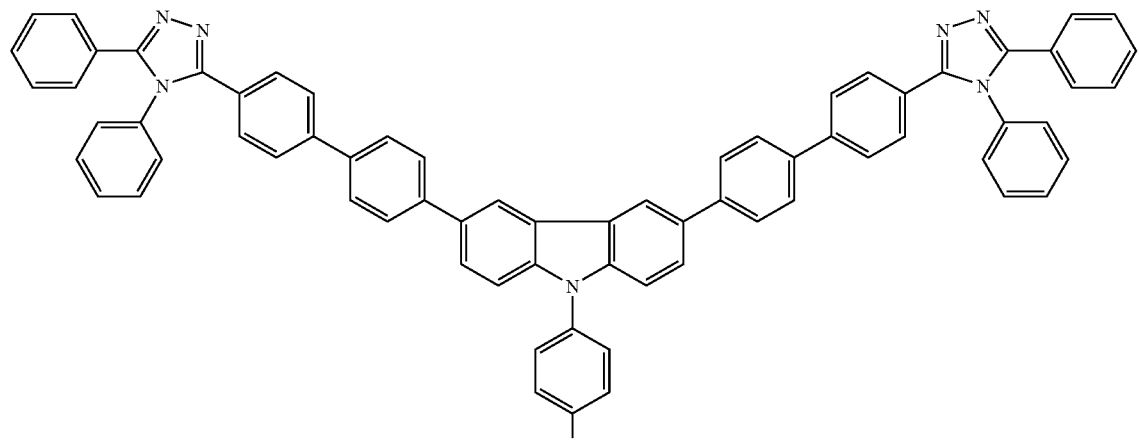
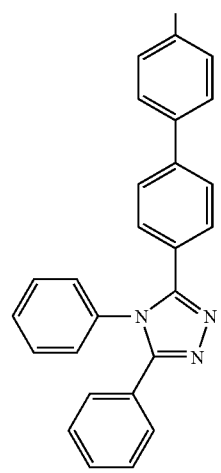
Formula 11
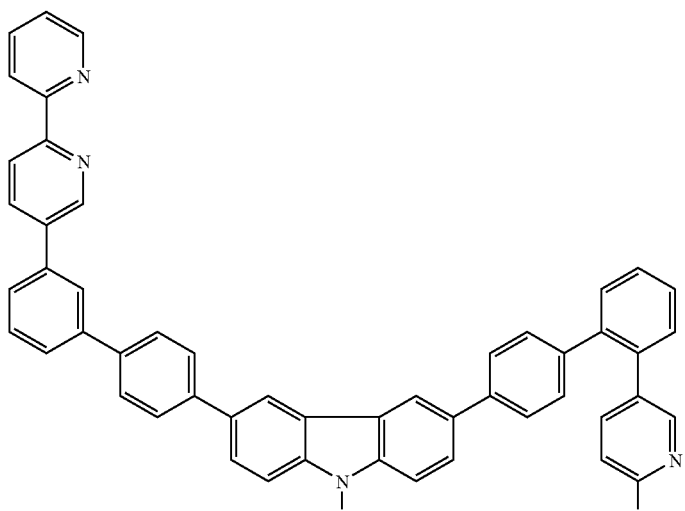

-continued

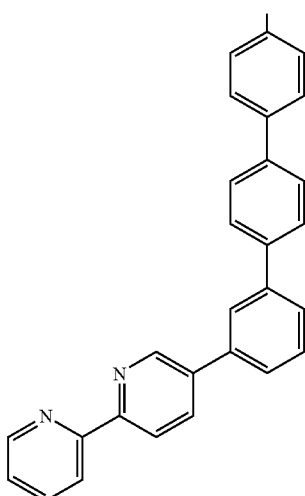
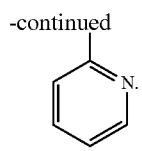

8. An organo-electroluminescent device comprising:
a first electrode;
a second electrode; and
at least one layer interposed between the first electrode and the second electrode,
wherein the at least one layer comprises a carbazole compound represented by Formula 1:

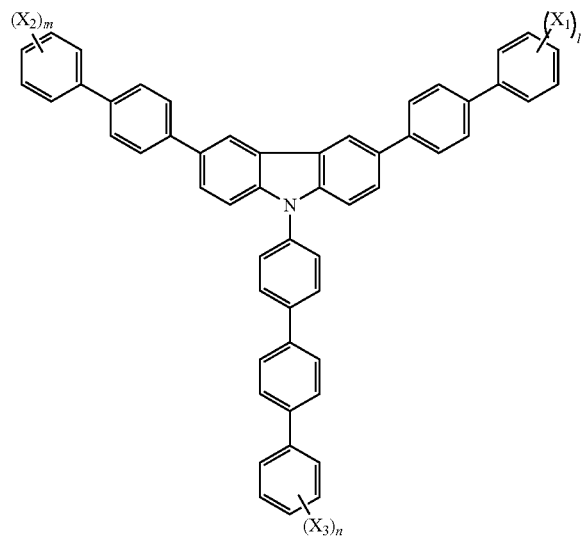

wherein $X_1$, $X_2$ and $X_3$ are each independently selected from the group consisting of a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 1 to 5.

9. The organo-electroluminescent device of claim 8, wherein the layer comprising the carbazole compound is an emission layer.

10. The organo-electroluminescent device of claim 8, wherein the layer comprising the carbazole compound is a hole transport layer or a hole injection layer.

11. A method of manufacturing an organo-electroluminescent device, the method comprising:
disposing a layer between a first electrode and a second electrode, wherein the layer comprises a carbazole compound represented by Formula 1:

Formula 1

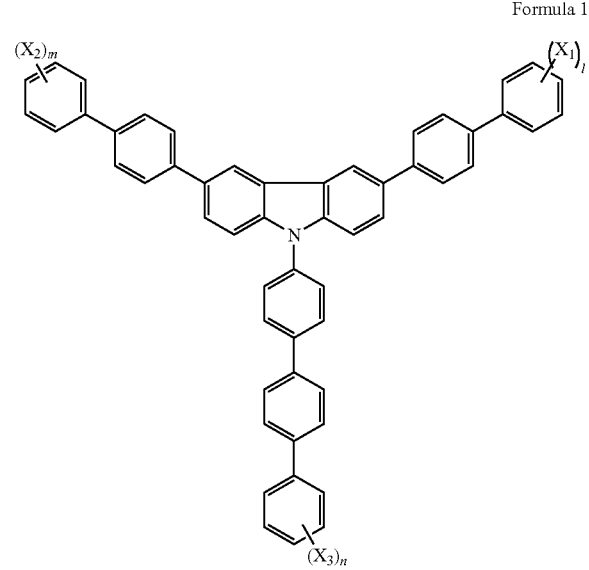

wherein $X_1$, $X_2$ and $X_3$ are each independently selected from the group consisting of a substituted or unsubstituted $C_6$-$C_{30}$ aryl group, a substituted or unsubstituted $C_6$-$C_{30}$ arylalkyl group, a substituted or unsubstituted $C_2$-$C_{30}$ heteroaryl group, a substituted or unsubstituted $C_3$-$C_{20}$ cycloalkyl group and a substituted or unsubstituted $C_5$-$C_{30}$ heterocycloalkyl group; and l, m and n are each independently an integer from 1 to 5.

* * * * *